(12) United States Patent
Katayama

(10) Patent No.: US 8,007,436 B2
(45) Date of Patent: Aug. 30, 2011

(54) BIOLOGICAL INFORMATION MONITORING SYSTEM

(75) Inventor: Noritada Katayama, Yokohama (JP)

(73) Assignee: Intellectual Property Bank Corp., Tokyo (JP)

( * ) Notice: Subject to any disclaimer, the term of this patent is extended or adjusted under 35 U.S.C. 154(b) by 400 days.

(21) Appl. No.: 10/552,509

(22) PCT Filed: Apr. 9, 2004

(86) PCT No.: PCT/JP2004/005130
§ 371 (c)(1),
(2), (4) Date: Oct. 5, 2005

(87) PCT Pub. No.: WO2004/089202
PCT Pub. Date: Oct. 21, 2004

(65) Prior Publication Data
US 2007/0043304 A1 Feb. 22, 2007

(30) Foreign Application Priority Data

Apr. 10, 2003 (JP) ................................. 2003-106630

(51) Int. Cl.
*A61B 5/02* (2006.01)
*A61B 5/00* (2006.01)
(52) U.S. Cl. ........ 600/301; 600/300; 600/481; 600/549; 128/920; 703/2; 703/3
(58) Field of Classification Search .......... 600/300–301, 600/363–365, 373–374, 377–379, 382–384, 600/386–394, 481, 485, 500–503, 509, 515–519, 600/529–531, 544–547, 549; 128/903–905, 128/920; 705/2–3
See application file for complete search history.

(56) References Cited

U.S. PATENT DOCUMENTS

| 3,651,694 A | * | 3/1972 | Lamb ........................... 374/114 |
| 3,699,813 A | | 10/1972 | Lamb |
| 4,517,986 A | | 5/1985 | Bilgutay |

(Continued)

FOREIGN PATENT DOCUMENTS

EP 0 770 349 5/1997

(Continued)

OTHER PUBLICATIONS

Third Chinese Office Action dated Jul. 4, 2008 issued in connection with Chinese Patent Application No. 200480009621.0 corresponding to the present U.S. application. (with English translation).

(Continued)

*Primary Examiner* — Sam Yao
*Assistant Examiner* — Marie Archer
(74) *Attorney, Agent, or Firm* — Wenderoth Lind & Ponack, L.L.P.

(57) ABSTRACT

A biological information monitoring system includes a plurality of biological information sensor modules 1A and 1B attached to the right side and left side of a subject body, which sensor modules 1A and 1B each incorporate a biological information sensor for detecting biological information, and a communicator capable of wireless radio communication for the biological information. At least one of the biological information sensor modules 1A and 1B includes a determination device for performing determination of an abnormality by comparing the biological information detected by one biological information sensor in one of the sensor modules with biological information sent from the other biological information sensor module through the communicator.

7 Claims, 14 Drawing Sheets

U.S. PATENT DOCUMENTS

| | | | |
|---|---|---|---|
| 4,669,485 A * | 6/1987 | Russell | 600/492 |
| 5,218,962 A | 6/1993 | Mannheimer et al. | |
| 5,544,649 A | 8/1996 | David et al. | |
| 5,724,980 A * | 3/1998 | Nakamura et al. | 600/492 |
| 5,862,803 A * | 1/1999 | Besson et al. | 600/508 |
| 6,238,354 B1 * | 5/2001 | Alvarez | 600/549 |
| 6,344,025 B1 * | 2/2002 | Inagaki et al. | 600/490 |
| 6,511,437 B1 | 1/2003 | Nakamura et al. | |
| 2002/0045836 A1 | 4/2002 | Alkawwas | |
| 2003/0224685 A1 * | 12/2003 | Sharma | 442/304 |

FOREIGN PATENT DOCUMENTS

| | | |
|---|---|---|
| JP | 9-122083 | 5/1997 |
| JP | 9-192108 | 7/1997 |
| JP | 3040341 | 3/2000 |
| JP | 2001-137196 | 5/2001 |
| WO | 01/78577 | 10/2001 |

OTHER PUBLICATIONS

Wu, S. "Comparison and analysis of the difference between the left and right axillary temperatures of 170 stroke patients", Journal of Nursing Science, vol. 2, pp. 80-81, (1990). (with English translation).

Wang, et al. "Study on blood pressure difference between the left and right brachial arteries of patients suffering from hemiplegia due to cerebrovascular disorders", Journal of Brain and Nervous Diseases, vol. 4(3), pp. 177-178, (1996). (with English translation).

Supplementary European Search Report issued Apr. 16, 2009 in corresponding European Application No. 04726797.6.

D'Souza, et al., "Diagnosis and Management of Stenotic Aorto-Arteriopathy in Childhood," The Journal of Pediatrics, Jun. 1998, pp. 1016-1022.

Official communication dated Dec. 23, 2009 issued in corresponding European Patent Application No. 04 726 797.6.

* cited by examiner (12)

BIOLOGICAL INFORMATION MONITORING SYSTEM

TECHNICAL FIELD

This invention relates to a biological information monitoring system for detecting biological information such as the body temperature, pulse and blood pressure to determine the presence or absence of biological abnormality.

BACKGROUND ART

In general, diagnostic detection of biological information such as the body temperature, pulse and blood pressure has been so far performed to examine the physical abnormality based on the physical detection findings. The detection of biological information has been commonly made with a biological information sensor connected to a subject undergoing a medical examination by a physician or nurse. For example, the biological information can be gathered by measuring the body temperature of the subject with a thermometer placed under the armpit of the subject for a few minutes or measuring the pulse or blood pressure over time.

However, the biological information thus obtained by the inspection method as mentioned above is provisional data from which the biological condition of the subject cannot be fully perceived. Therefore, if the subject has subjective symptoms of abnormalities of some sort, there are cases where the physician or nurse cannot find the abnormality of the subject even by reviewing data obtained from biological tests and possibly fails to give an accurate diagnosis. Specifically in a case of irregular heartbeat or heartbeat abnormality, the abnormalities are not always manifested, and there is a possibility of failing to make an exact diagnosis of the abnormalities depending on conditions such as the psychological state of the subject and the time-span of inspection in a brief observation.

Such being the case, it is recommendable to continue observations of a subject with suspected physical abnormalities for a long stretch of time including sleep hours.

For instance, there are several recommended ways to conduct determination of abnormalities by using a small and light-weight biological information sensor attached to the body of the subject and a data analyzing device receiving data detected by the information sensor by wireless radio communication. In this case, there have been some few advances to use a sensor module incorporating the biological information sensor and transmitter and reduce the sensor module in size and weight so as not to cause limitation in physical activity of the subject.

By way of example, Japanese Patent Application Publication HEI 10-155749 discloses a "system for monitoring and informing about human health conditions" using a life sensor attachable to the human body to measure information on a living body such as pulse, motion, sounds and body temperature in real time. This conventional system is operated in conjunction with a system for alerting a caretaker on the basis of the information detected by the life sensor. The life sensor may be made like a wristwatch and incorporate a communication means, in concert with which a monitoring center is provided with a counterpart communication means to call back.

An "abnormal symptom detector and abnormality warning system" disclosed in Japanese Patent Application Publication No. 2000-93398 is provided with a skin stretch-shrink detection sensor for detecting the stretching and shrinking of the skin associated with pulsebeat and breathing, and an alert circuit for warning of an abnormality when detecting the abnormality. As the skin stretch-shrink detection sensor, a strain gauge is used. A telephone communication system is taken advantage of when detecting any abnormality.

Further, an "emergency relief system" disclosed in Japanese Patent Application Publication HEI 6-242206 has a sensor incorporated therein or connected thereto for detecting pulse, blood pressure and body temperature. This system incorporates a wristwatch transmitter capable of emitting faint radio waves, a receiver for receiving the emergency radio waves from the transmitter, a radio relay device having functions of transmitting and receiving the emergency radio waves, and a radio station for detecting the position of the radio relay device from the emergency radio waves from the radio relay device.

Japanese Patent Application Publication No. 2001-353130 discloses a "physical information detector" having a housing case incorporating a sensor for detecting the physical information and an output means. This detector is formed in a bow so as to be detachably retained on the auricle of a measuring subject. The detector of the same type may be formed like a pendant.

Japanese Patent Application Publication No. 2003-24287 discloses a monitoring device for body conditions, which includes a movement sensor (for measuring at least one of acceleration velocity and angular velocity), and a pulse sensor, so that the body conditions can be monitored by computing data from the sensors. The sensor for detecting the angular velocity is a gyro for detecting the angular velocity of the movement about the Z-axis perpendicular to the longitudinal direction and transverse direction of the superior or inferior limb, which is attached to the superior limb or inferior limb of a living body. The monitoring device further has pulse calculating means with denoising means for filtering out noises in the output from the pulse sensor when issuing pulse output from the acceleration sensor.

The measuring devices according to the conventional technologies described above all are featured by the form and shape of each sensor, detecting method, communication means and emergency system and in that the biological information sensor (including a thermometer, pulse sensor and/or blood pressure meter) is placed at one location of the body of the subject being monitored to collect the biological information. However, the conventional measuring devices generally check up on whether the measurement results obtained from the biological information thus detected for making abnormality determination fall within a predetermined normal range (e.g. body temperature of 36.0° C. to 36.9° C., pulsebeat of 60 to 80 beats per minute, systolic blood pressure of 100 to 120 mmHg, and diastolic blood pressure of less than 80 mmHg may be roughly determined as the basis for average adults at rest.)

However, the conventional methods have a common major problem. That is, it is not always possible for the conventional methods to detect some kinds of abnormalities from the biological information obtained from only one portion of the living body, although some abnormalities may be recognized on the basis of the biological information detected from more than one portion of the living body.

For instance, a physical abnormality may not appear in body temperature on one of the right and left sides of the body, even if an abnormality in body temperature on the other side of the body appears. In such a case, the side of the body, which has abnormal body temperature, may not possibly be diagnosed as the physical abnormality. In fact, there is a case where only the body temperature on one side of the body, which is getting paralyzed, is reduced before the subject who undergoes any diagnosis and is developing disorder is aware of a subjective symptom during a precursory symptom of cerebral infarction, whereas the body temperature on the other nonparalyzed side of the body may change little within the normal range. The physical abnormalities cannot be assuredly recognized by one-point measurement for biological information in which the biological information is detected at one portion of the subject body, possibly resulting in retarding early detection of dangerous diseases.

The physical abnormalities do not appear on both the right and left sides of the body as abnormalities in physical information (e.g. body temperature), but they may sometimes appear as a difference in physical information on both sides of the body (e.g. difference in body temperature). For instance, there may possibly be a difference in body temperature between the right and left sides of the body due to the abnormality of the body in spite of both the temperatures taken under the armpit of the right and left sides of the body falling within the normal temperature range when the subject has an abnormality of the body. In such a case, the physical information must be gathered from the multiple loci of the body to find the abnormality promptly.

To be more specific, it was impossible or difficult to recognize a certain type of physical abnormality by the conventional methods in which biological information was generally detected only at one portion of the subject body, to consequently cause delay in finding the abnormality. As a result, the conventional methods could not apply to early treatment upon finding jeopardy of the subject undergoing medical examination at the early stage. For instance, cerebral stroke and myocardial infarction were difficult to find in their early stages on the basis of the biological information such as body temperature detected at only one portion of the subject body.

In the light of the conventional circumstances as described above, the present invention seeks to provide a biological information monitoring system capable of detecting biological information from the multiple loci of the right and left sides of the living body to early determine physical abnormalities with higher accuracy than that of the conventional art.

DESCRIPTION OF THE INVENTION

To attain the object described above according to the present invention, there is provided a biological information monitoring system comprising a plurality of biological information sensor modules attached to the right side and left side of a subject body, which sensor modules each incorporate a biological information sensor for detecting biological information, and a communication means capable of wireless radio communication for the biological information. At least one of the biological information sensor modules includes a determination means for performing determination of an abnormality by comparing the biological information detected by one biological information sensor in one of the sensor modules with biological information sent from the other biological information sensor module through the communication means.

DETAILED DESCRIPTION OF THE INVENTION

Figure 1:
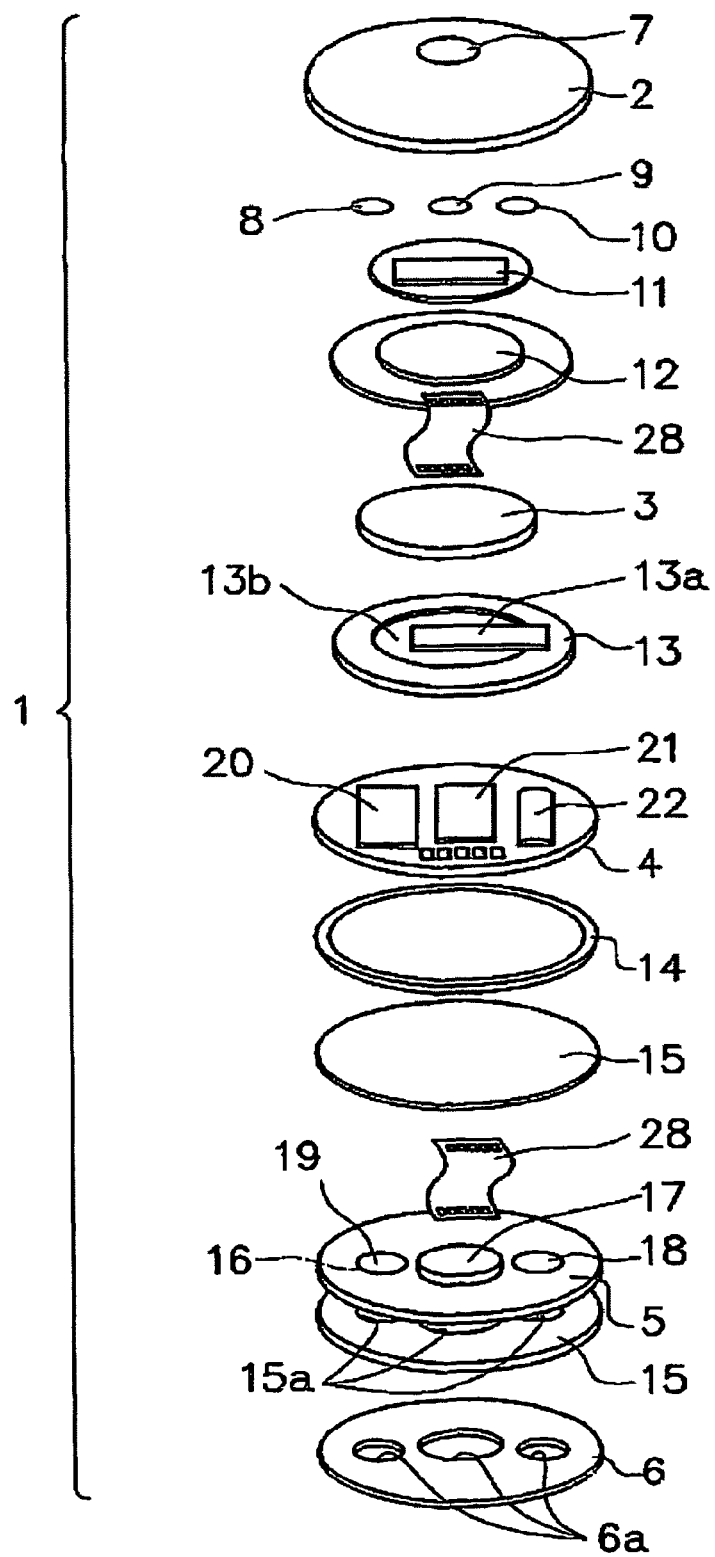
FIG. 1 is an exploded perspective view showing a biological information sensor module in one embodiment of the present invention.
Figure 2:
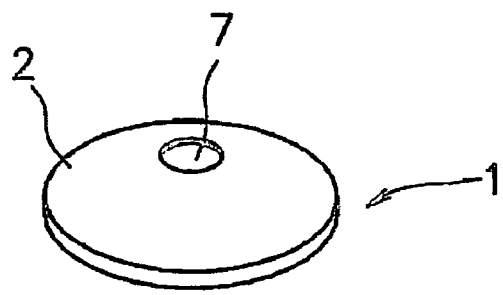
FIG. 2 is a perspective view showing the biological information sensor module shown in FIG. 1.
Figure 3:
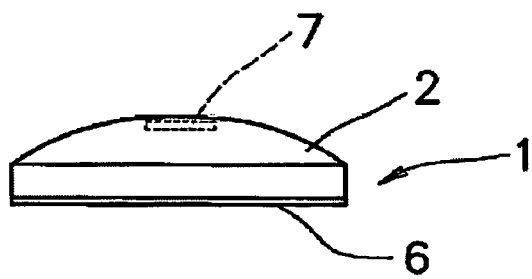
FIG. 3 is a front view of the module shown in FIG. 2.
Figure 4:
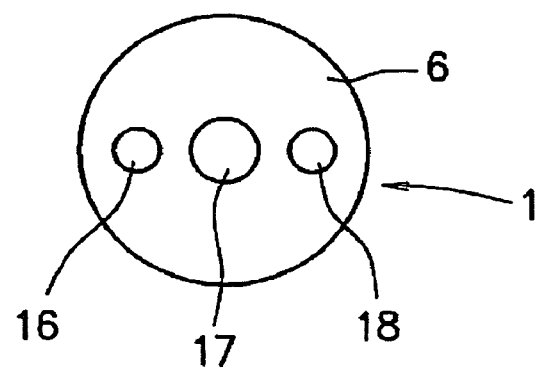
FIG. 4 is a bottom view of the module shown in FIG. 2.

The biological information monitoring system according to the present invention comprises a plurality of biological information sensor modules attached to the right side and left side of a subject body. The sensor modules each incorporate a biological information sensor for detecting biological information, and a communication means capable of wireless radio communication for the biological information. At least one of the biological information sensor modules includes a determination means for performing determination of abnormality by comparing the biological information detected by the biological information sensor in the sensor module with biological information sent from another biological information sensor module through the communication means.

The biological information detected by the biological information sensor includes body temperature, pulse, blood pressure and so forth.

It is adequate that the state of temperature difference not lower than 0.5° C., pulse difference not less than 7 beats per minute, and blood pressure difference not less than 10 mmHg are determined as abnormal by using the determination means.

The biological information sensor module may be provided with an alert means for issuing a warning when the determination means detects the abnormality.

One of the biological information sensor modules may have a communication means capable of communicating with the outside to release the determination result of the determination means, and correspondingly, an external electronic device capable of receiving the determination result outputted from the communication means may be prepared outside the sensor module.

Further, at least one of the biological information sensor modules may be provided with a memory for storing at least one of the determination result outputted from the determination means and the biological information measured by the biological information sensor, so that the measured biological information can be accumulated.

There may be used an electronic device for transmitting data to the biological information sensor module by wireless radio communication, so that the determination means can perform abnormality determination with reference to the data sent from the electronic device.

The aforementioned communication means for outside communication can deliver identification signals for distinguishing individual living subjects each having the biological information sensor module based on the determination result data thus obtained through wireless radio communication. The external electronic device in this case can figure out the identification signals and the determination result data sent from the communication means, to thus identify the individual living subjects.

The "radio communication" here is a generic term used to refer to radio transmission and reception. That is, this term further includes communication exchanged between radio transmitter and receiver sets, which is performed while executing error processing.

The embodiments of the present invention will be described hereinafter in detail.

FIGS. 1 through 4 show the biological information sensor module 1 in the first embodiment of the biological information monitoring system of the invention. The biological information sensor module 1 has a housing case 2 incorporating a battery 3, a main board 4 and a sensor board 5. On the bottom surface of the module, there is placed a two-sided adhesive tape 6 having air permeability and nonallergenic potency so as to attach the sensor module directly to the living body. To be more specific, the housing case 2 is formed of synthetic resin in a hollow bowl-like shape having a bottom opening and made small (e.g. about 37 mm in diameter and 7.2 mm in thickness). The housing case is provided on the upper portion thereof with a reset switch 7. Into the inside of the housing case 2, there are placed, in order, three environment sensors, i.e. an ambient temperature sensor 8, a barometric sensor 9, and a humidity sensor 10. Further, the housing case 2 incorporates a chip antenna 11 for communication, a tilt sensor 12, the battery 3 (e.g. button type lithium battery), a battery holder 13, the main board 4, an electromagnetic wave shielding plate 14, and a perforated protect cover 15. The sensor board 5 and perforated protect cover 15 are fixed so as to cover the bottom of the housing case 2. The two-sided adhesive tape 6 adhering onto the perforated protect cover 15 has apertures 6A. The term "inside" is here used to refer to the inner surface side of the housing case 2 (upper side of FIG. 1), and the "outside" to the open bottom side of the housing case 2 (lower side of FIG. 1).

Next, each component of the aforementioned biological information sensor module 1 will be described. The module in this embodiment includes the sensor board 5, and three biological information sensors, i.e. temperature sensor 16, heartbeat meter 17 of a water-resistant microphone, and pressure/pulse sensor 18 (e.g. an optical sensor based on Japanese Patent Application Publication HEI 7-8 8090).

These biological sensors (temperature sensor 16, heartbeat meter 17 of a water-resistant microphone, and pressure/pulse sensor 18) each have a detection probe exposed to the outside (lower side of FIG. 1) through an aperture (not shown) in the sensor board 5. The inner surface (upper side surface of FIG. 1) of the temperature sensor 16 is shielded by a heat insulator 19 to keep out the heat generated from the electronic circuits on the main board 4. The exterior side surface of the sensor board 5 is covered with the perforated protect cover 15. Although the two-sided adhesive tape 6 is attached to the outer surface of the sensor board 5 as mentioned above, the detection probes of the biological sensors (temperature sensor 16, heartbeat meter 17 of a water-resistant microphone, and pressure/pulse sensor 18) are exposed outside through the apertures 15A in the protect cover 15 and the apertures 6a in the two-sided adhesive tape 6 (see FIG. 4).

The biological information sensor described above should not be understood as being limitative, in that other known sensors or other techniques can be used, and therefore, will not be described in detail again. A low consumption, small and lightweight sensor capable of being powered by a battery 3 and performing long-term detection of biological information with high accuracy may be used as the biological information sensor.

On the main board 4 put on the sensor board 5, there are mounted a main integrated circuit 20 including a measurement calculating unit (determination means), a control unit (CPU) and a memory (data storing means), a radio communication integrated circuit 21, and a vibrator 22 serving as warning means. On the outer side surface of the main board 4, there are disposed the electromagnetic wave shielding plate 14 with a slight concave, which is made of metal for eliminating the harmful effects of electromagnetic waves, and the perforated protect cover 15. The memory has not only a function of storing basic data for performing various kinds of determination as described later and identifying signals for assigning individual subjects, but also a calendar function and a timer function.

The battery holder 13 on the inner side of the main board 4 can also serve as a protective cover. On the outer side surface of the battery holder, an analog circuit such as an amplifier is mounted, although not shown in the accompanying drawings. The battery holder 13 has a pair of electrodes 13a and 13b in contact with the electrodes of the battery 3. The button type battery 3 is removably set in the battery holder 13.

The tilt sensor 12 on the inside of the battery holder 13 and battery 3 serves to detect the posture of the subject with the biological information sensor module 1. The structure of the tilt sensor 12 will be described with reference to FIG. 3. A substantially conical rotating disc 24 formed like a spinning top is rotatably and swingably supported by a shaft 23a on a tilt sensor housing 23. On a part of the top-like rotating disc 24, there is mounted a weight 25 for making the gravity point eccentric. The back of the top-like rotating disc 24 is colored to form monotone gradations. A light emitting element 26 such as an LED (light-emitting diode) and a pair of light-sensitive elements 27a and 27b such as a photodiode are placed opposite to the top-like rotating disc 24 on the tilt sensor housing 23.

In the biological information sensor module 1 attached to the subject to be monitored, the weight moves in the direction of gravitational force according to the posture of the subject, to consequently move the top-like rotating disc 24 by a corresponding angle. The light emitting element 26 and the light-sensitive elements 27a and 27b are fixed on the tilt sensor housing 23 so as not to move relative to the body of the subject, so that the top-like rotating disc 24 can rotate relative to the light emitting element 26 and the light-sensitive elements 27a and 27b. The light emitted from the light emitting element 26 is reflected on the back of the top-like rotating disc 24 toward the light-sensitive elements 27a and 27b. The light-sensitive elements receive the reflected light to measure the light intensity of the reflected light. Since the back of the top-like rotating disc 24 is colored to form monotone gradations, the light intensity of the reflected light depends on the point at which the light from the light emitting element 26 reflects on the back of the top-like rotating disc 24. Accordingly, the posture (rotation angle) of the top-like rotating disc 24 can be determined from the intensity data of the lights detected by the light-sensitive elements 27a and 27b with reference of database prescribed on the relation between the position of the weight 25 and the tone gradation pattern of the top-like rotating disc 24.

Figure 7:
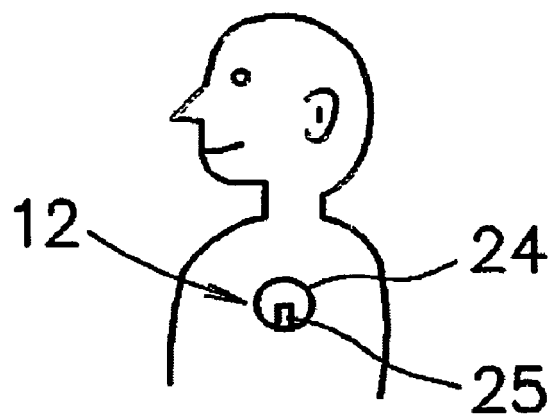
FIG. 7 illustrates a subject to be monitored with the tilt sensor of FIG. 5 in an erect posture.
Figure 8:
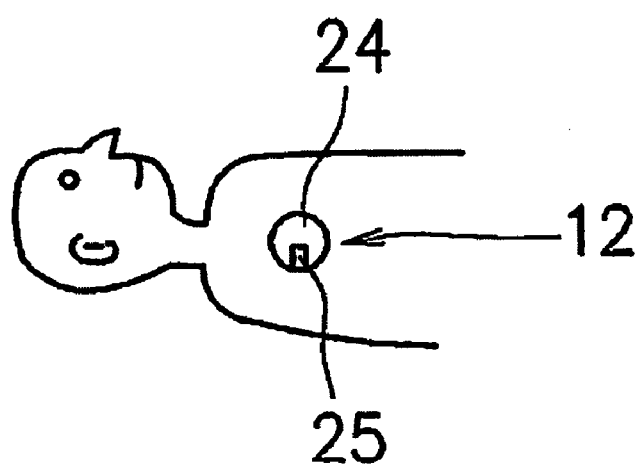
FIG. 8 illustrates a subject to be monitored with the tilt sensor of FIG. 5 in a recumbent posture.

The position and attitude of the biological information sensor module 1 with respect to the vertical direction vary with whether the subject with the biological information sensor module is in an erect posture (FIG. 7) or in a recumbent posture (FIG. 8). Following this, the position of the weight 25 is changed to eventually change the rotation angle of the top-like rotating disc 24 with the weight 25. As a result, the position in the black part of the gradation pattern of the back of the top-like rotating disc 24 is changed relative to the light emitting element 26 and light-sensitive elements 27a and 27b, to thereby determine the position of the top-like rotating disc 24 with respect to the vertical direction from the intensity of the light detected by the light-sensitive elements 27a and 27b. That is, the posture of the subject with the biological information sensor module 1 can be recognized, namely, it turns out whether the subject is in an erect posture or in a recumbent posture. Furthermore, the tilt sensor 12 makes it possible to deter the postural change of the subject when turning over. Since the detection of the posture of the subject with the tilt sensor 12 does not require special accuracy, the aforementioned structure of the tilt sensor suffices as a means for detecting the tilt of the subject body.

The reset switch 7 on the housing case 2 is a button switch operable from the outside of the housing case, so that the subject can cancel a vibration alert or other warning notice. The reset switch 7 may be disposed in a depression so as to prevent erroneous operation of the switch. The reset switch 7 may be configured so as to be switched on a few seconds after being depressed.

The components incorporated in the housing case 2, i.e. the biological information sensor (temperature sensor 16, heartbeat meter 17 and pressure/pulse sensor 18), main integrated circuit 20, radio communication integrated circuit 21, vibrator 22, tilt sensor 12, chip antenna 11, environment sensors (ambient temperature sensor 8, barometric sensor 9 and humidity sensor 10), and a reset switch 7, are adequately connected on a flexible joint board 28 or the like. The battery 13 is in contact with electrodes 13a and 13b on the battery holder 13. The aforementioned components are supplied with power from the battery 3 and controlled by the CPU on the main integrated circuit 20, so that data can be transferred between the main integrated circuit 20 and memories. The circuitry design applicable to the sensor module of the invention is generally known in the art of this field, and therefore, may have any other desired circuit. Thus, the circuitry in this invention is by no means limitative and will not be described here in detail. Also, the kinds and structures of the environment sensors and biological information sensors are not to be considered limited to the illustrated forms and may be altered adequately or combined variously as the occasion arises.

Next, the biological information monitoring system formed of the aforementioned biological information sensor module 1 will be described with reference to FIG. 9 and FIG. 10.

In one embodiment of the invention, two biological information sensor modules 1 as described above (for the sake of simplicity, one of the sensor modules is marked as "1A", and the other sensor module is marked as "1B") are attached one to the right side of the subject body and the other to the left side of the subject body. The sensor modules should be located at symmetric points (e.g. armpits) on the right and left sides of the subject body. The sensor modules (temperature sensor 16, heartbeat meter 17 and pressure/pulse sensor 18) have to be fixed onto the subject body so as to bring the detection probes of the sensors into firm contact with the subject body by using two-sided adhesive tapes 6 (Step S1). Then, the temperature sensor 16 is operated to measure the temperature of the subject, the heartbeat meter 17 is operated to measure the heartbeat of the subject, and the pressure/pulse sensor 18 is operated to measure the blood pressure and pulse of the subject under the control of the CPU of the main integrated circuit 20 with supply of electric power from the battery 3 (Step S2). While detecting four kinds of the biological information (body temperature, heartbeat, blood pressure and pulse), determination of the posture of the subject to be monitored (whether the subject is in an erect posture or in a recumbent posture) is carried out by use of the tilt sensor 12, and simultaneously, the ambient temperature, barometric pressure and humidity are measured with the ambient temperature sensor 8, barometric sensor 9 and humidity sensor 10, respectively (Step S3).

The four kinds of biological information (body temperature, heartbeat, blood pressure and pulse) detected by the temperature sensor 16, heartbeat meter 17 and pressure/pulse sensor 18, ambient information (ambient temperature, barometric pressure and humidity), and the data of the posture of the subject and time, and/or biological information are stored in the memory of the main integrated circuit 20 since starting the measurement (Step S4). Then, determination of whether each biological information falls within a pertinent numeric range is performed in the measurement calculating unit (Step S5). Since it is desirable to provide the pertinent numeric range for each of the erect posture (active state) and recumbent posture (resting state) of the subject, detection values measured by the tilt sensor 12 should be compensated according to the posture of the subject to be monitored.

Concurrently, the measured biological information is exchanged by wireless between the biological information sensor modules 1A and 1B by using the radio communication integrated circuit 21 and drip antenna 11 (Step 6). The biological information data measured directly by the biological information sensor module (temperature sensor 16, heartbeat meter 17 and pressure/pulse sensor 18) incorporated in one of the biological information sensor modules (e.g. module 1A) are compared with the biological information data transmitted from the other biological information sensor module (e.g. module 1B). Thus, upon obtaining a difference between the two sets of biological information detected by the biological information sensor modules 1A and 1B, determination of whether the difference falls within the pertinent numeric range is performed (Step S7).

In this embodiment, in addition to the determination of whether the biological information measured by the biological information sensor module (temperature sensor 16, heartbeat meter 17 and pressure/pulse sensor 18) in Step 5 per se is pertinent or not, which is performed for checking a physical abnormality of the subject to be monitored, the determination of whether the difference in biological information between the right and left sides of the subject to which the paired biological information sensor modules 1A and 1B are attached is performed in Step 7 for further checking the physical abnormality of the subject. The benefits of using the paired biological information sensor modules will be described later.

When determining the measurement results obtained in Step 5 and Step 7 as normal, a sequence of monitoring processes is finished. However, when at least one of the measurement results obtained in Step 5 and Step 7 is determined as abnormal, the CPU in the main integrated circuit 20 is operated to drive the vibrator 22, so that the subject being monitored can receive an alert (Step S8). At the same time, an abnormality signal is transmitted from the radio communication integrated circuit 21 through the chip antenna 11 by wireless (Step S9). Along with the abnormal signal thus issued, the identification signal (ID signal) for identifying the subject with the biological information sensor modules is issued. When a host computer 29, which is an electronic device installed remotely from the subject, receives the abnormality signal created in Step 9 together with the ID signal, the abnormality of the subject with the biological information sensor modules can be recognized (Step S 10). Thus, a sequence of monitoring processes is finished. However, since the monitoring of the biological information is generally carried out continuously for a long stretch of time in this embodiment, the sequence of monitoring processes is continued without interruption.

Thus, the subject being monitored can be aware of the subject's own abnormality with the warning vibrations generated by the vibrator 22, to thus enable immediate action in Step S8. Also in Step 10, the physician or nurse in attendance can promptly recognize and cope appropriately with the abnormality of the monitored subject with the host computer 29.

Since the biological information such as the body temperature and pulsebeat on the respective right and left sides of the subject body can be detected separately, a partial change in physical condition of the subject being monitored may possibly be perceived from the abnormality thus detected. Further, the biological information can be detected separately on the right and left sides of the subject body to recognize the abnormality from the difference in biological information on the right and left sides of the subject body, so that early recognition and precaution of the physical abnormality, which were difficult in the past by measuring mere biological information, can be realized.

Here, the benefits of using the biological information sensor modules are described. In the early stage which causes apoplexy and myocardial infarction, there is a case where a patient has no subjective symptom, but any physical abnormality may possibly be developed as time passes, resulting in paralysis on one side of the patient's body or the death of the patient. Even in the early state where the patient is aware of subjective symptoms, some changes in biological information such as the body temperature, pulse or blood pressure must have taken place in the one side of the body, which became paralyzed in a later stage, but such disorders cannot possibly be recognized merely by detecting the biological information at one portion of the subject body. That is, accurate determination of the biological information cannot be expected because only either of normal biological information or abnormal biological information can be detected from either of the not-paralyzed portion and the paralyzed portion of the body. Based on the biological information detected from the paralyzed portion, the biological information data values can but be considered as a little high or low, to thus be improperly determined to fall within the normal range. Meanwhile, according to the embodiment of the invention, any physical disorders can be recognized by detecting the difference in body temperature between the right and left sides of the subject body, even if the biological information, e.g. body temperature, falls within the normal range. For instance, assuming that the body temperature of the right side of the body is 35.8° C. and that of the left side of the body is 36.8° C., these body temperatures per se may be considered as just about normal, but the difference of 1° C. in body temperature between the right and left sides of the body is thought to be possibly caused by any physical abnormality. In such a case, the physical abnormality cannot be found by the conventional method of detecting the biological information at only one portion of the subject body, whereas the embodiment of the invention described above makes it possible to find the physical abnormality without a specific thorough inspection. Although the measurement of the body temperature was described above as one example of the embodiment of the invention, the physical abnormalities can of course be found from the pulsebeat, blood pressure or other biological information in the same manner as above. In the case of performing the abnormality determination based on the pulsebeat or blood pressure, criteria for determining the biological information as abnormal may preferably be specified such that a difference in pulsebeat between the right and left sides of the body is 7 or more beats per minute and a difference in blood pressure is 10 mmHg or above between the same.

Table 1 shows collectively the absolute criteria of the body temperature, pulsebeat and blood pressure and the criteria for discerning physical abnormality from the difference in the biological information of the right and left sides of the subject body.

TABLE 1

|  | Normal case | Caution needed | Case deemed as abnormal | Remarks |
| --- | --- | --- | --- | --- |
| Body temperature | 36.0~36.9° C. | 37.0~37.9° C. | Less than 36.0° C. 37.0° C. or more | <Average temperature> |
| Difference in temperature between right and left body sides | Less than 0.2° C. | 0.2~0.5° C. | 0.5° C. or more | Baby: 37.0° C. Average adult: 36.0 to 36.9° C. The aged: 36.0° C. |
| Pulsebeat | 60~80 bpm | Less than 60 bpm 90 bpm or more | Less than 50 bpm 100 bpm or more | Bradycardia: 50 bpm or less |
| Difference in pulsebeat between right and left body sides | 0~3 bpm | 3~6 bpm | 7 bpm or more | Tachycardia: 100 bpm or more |
| Blood pressure | (S) 100~120 mmHg (D) 80 mmHg or below | (S) 120~140 mmHg (D) 80~90 mmHg | (S) 140 mmHg or above (D) 90 mmHg or above | (S) Systolic pressure (D) Diastolic pressure |

TABLE 1-continued

| | Normal case | Caution needed | Case deemed as abnormal | Remarks |
|---|---|---|---|---|
| Pulse pressure (Pressure difference) | 40 ± 10 mmHg | 30 mmHg or above 60 mmHg or above | 20 mmHg or above 100 mmHg or above | |
| Difference in pressure between right and left body sides | Less than 3 mmHg | 3~10 mmHg | 10 mmHg or above | |

For instance, a patient may not notice symptoms in the early stage of ischemic disease, which causes cerebral apoplexy and myocardial infarction, and then, complains of any physical abnormality shortly before facing a dangerous situation in an advanced stage of symptoms, and is not infrequently admitted to a hospital emergency room after going into dangerous situations.

Thus, in the early stage where subjective symptoms are difficult to ascertain in general, the biological information such as the body temperature, pulsebeat and blood pressure detected by the one-point measurement for biological information is not determined as abnormal unless the absolute value of the biological information is significantly unusual. That is, a patient having an unusual value of the biological information should be aware of any subjective symptoms. Therefore, the one-point measurement for biological information is not an effective means from the aspect of the need for giving an early warning before apparently displaying symptoms.

In this behalf, the monitoring system of the invention makes it possible to recognize physical abnormalities of the patient being monitored before the patient complains of any subjective symptom by detecting the difference between the body temperatures on the right and left sides of the patient body even when the biological information, e.g. body temperature, is within a normal range.

The monitoring by using the conventional biological information sensor issues a warning after coming into a stage appearing as an imminent danger or a dangerous situation, whereas the monitoring system of the invention can preliminarily give early warning of danger signs to not only the patient under inspection but also medical personnel, a family of the patient, care personnel or other persons concerned before the patient complains of any subjective symptom and comes into a stage appearing as an imminent danger or a dangerous situation, to thereby prevent the patient from developing a serious form of the disease.

In applying the monitoring system in this embodiment of the invention to the subject to be monitored, only the compact biological information sensor module 1 capable of exchanging data with the host computer 29 may simply be attached to the body of the subject, to continue the monitoring of the biological information while going about the usual daily life of the subject without feeling confined by the sensor module of the invention. The sensor module of the invention can be driven over several days to continuously monitor the biological information until the battery 3 runs out of power. Specifically, the sensor module can be operated throughout the night even at midnight at which physical abnormalities of the subject are liable to occur especially in fluctuation of the biological information, so that the physical abnormality can be recognized as soon as it occurs. The monitoring system can just immediately issue a warning to the subject with vibrations and the abnormality data to the outsiders by wireless when detecting the physical abnormality. If a patient suffering a stroke or cardiac infarction is in a coma without wearing the sensor module of the invention, the patient may not possibly be recovered. However, the patient relying on the monitoring system of the invention can avoid the risk of causing serious conditions by continuously monitoring the biological information of the patient or prevent severe disease in the patient with high probability. The alert means in the invention should not be understood as being limited to the vibrator 22 and any other warning means such as a buzzer may be used instead.

When detecting the physical abnormality, the abnormality signal is sent to the host computer 29 by wireless simultaneously with the vibration warning of the vibrator 22, so that a physician or nurse in charge of the host computer 29 can concurrently recognize the abnormality occurring in the patient and cope with the abnormal situation without undue delay. Since the ID signal for identifying the patient is sent with the abnormality signal, even more than one patient can be distinguishably identified with accuracy without causing confusion. In this regard, however, the conventional monitoring methods of this type required not only a huge amount of work for constantly monitoring a quantity of the biological information obtained from many subjects or patients, but also a large-scale monitoring system, and therefore, the conventional monitoring systems were not suitable for practical use at all. Unlike the conventional monitoring systems, the biological information monitoring system of the invention, which can easily be established only by the compact biological sensor module 1 to be attached directly to the subject body and the host computer 29. Although the host computer 29 can be applied for more than one patient, it may be only one common personal computer, consequently allowing the monitoring system of the invention to be constructed on a remarkably small scale and enable significant savings in labor of the physician or nurse in charge. Accordingly, the monitoring of a large number of subjects to detect the biological information data according to the biological information monitoring system of the invention can be concurrently performed more easily and more inexpensively than the conventional monitoring system.

Since the biological information data detected by the biological information sensors (temperature sensor 16, heartbeat meter 17 and pressure/pulse sensor 18) are stored in the memory of the main integrated circuit 20 in the biological information sensor module 1 of the invention, personal characteristics and predisponency of the biological information of the subject being monitored in the normal life of the subject can also be recognized regardless of the occurrence or non-occurrence of the physical abnormality. It is advantageous to store time data and/or environmental data along with the biological information data thus detected in the memory so as to facilitate posterior analysis of the biological conditions of the monitored subject.

The data stored in the memory can be shared with the related parties including the monitored subject, subjects family, care personnel, physician and nurse, so that the related parties all can share the same recognition concerning the physical conditions of the monitored subject. This routine of storing the biological information data thus obtained enables accurate diagnosis on the basis of the stored data even if an attending physician is changed, and specifically, makes it possible to continuously monitor the biological information over the long term to obtain highly reliable biological information data. The biological information data thus stored can be utilized effectively not only for future determination and evaluation of the physical abnormal conditions of the subject undergoing inspection, but also as reference data for care for abnormalities possibly caused. Meanwhile, the data shored in the memory may be transmitted to the host computer 29 by wireless to analyze the biological information on the side of the host computer 29. For instance, the biological information detected by the biological information sensor module 1 is sent into the host computer 29 in real time to observe the subject being monitored, while identifying the subject with the ID signal. Thus, the biological information monitoring system of the invention enables concurrent processing to send the biological information data to the host computer 29 in real time and to send the abnormality signal to the host computer 29 when detecting the abnormality. All kinds of the biological information are not necessarily stored in the memory, but only the result data of the abnormality detection may be stored in the memory for making data storage more rational.

One abnormality determination is performed in Step 5 in the aforementioned embodiment of the invention on the basis of the biological information data detected by the biological information sensor module 1, and another abnormality determination is performed in Step 7 on the basis of the difference between two sets of biological information detected by one pair of biological information sensor modules 1. Threshold values as criteria for these abnormality determinations may be set in advance in the memory of the main integrated circuit 16. The threshold values thus set may be compensated with human data of the subject's posture (erect posture or recumbent posture) detected by the tilt sensor 12, and ambient data of ambient temperature, barometric pressure and humidity detected by the environment sensors (ambient temperature sensor 8, barometric sensor 9 and humidity sensor 10). Alternatively, the threshold values may be severally determined by the physician or nurse in consideration of specific characteristics of the subjects undergoing inspection and transmitted from the host computer 29 to the biological information sensor module 1 by wireless so as to be stored in the memory of the main integrated circuit 20. In addition, the private information data such as the clinical history and medication history of the subject undergoing inspection may also be inputted from the host computer 29 into the memory of the main integrated circuit 20 in the biological information sensor module 1 via the wireless system. Also, the ID signal data may be inputted from the host computer 29 into the memory of the main integrated circuit 20 in the biological information sensor module 1 by wireless. The various data stored in the memory of the main integrated circuit 20 in the biological information sensor module 1 may be read out, written, revised and erased on the side of the host computer 29 through the wireless system.

The biological information sensor module 1 may be used as an alarm for letting the subject know the times for taking medicine, getting medical consultation, getting to bed and getting out of bed in conjunction with a timer function. As one alarm function of the biological information sensor module, the vibrator 22 may be actuated to vibrate in a different warning pattern from that in the case of warning of the physical abnormality. In addition to the vibrator, a buzzer or melody alarm, although not shown in the accompanying drawings, may be used.

The detection result of the posture of the subject detected by the tilt sensor 12 may be transmitted to the host computer 29 through the radio communication integrated circuit 21 and chip antenna 11. In doing so, a supervisor observing the host computer 29 can be aware of not only whether the subject is in an erect posture or in a recumbent posture, but also whether the subject rolls over in bed and the number of times of rolling over. For instance, when monitoring a solitary old person by the biological information monitoring system of the invention, the monitored person can be confirmed as alive from the rolling-over information thus detected. The number of times of rolling over may be considered to typify the physical features of the subject being monitored.

It is convenient to apply a Bluetooth system for the communication means of the biological information sensor module 1, i.e. the radio communication integrated circuit 21 and chip antenna 11, but this invention does not contemplate imposing any limitation on the communication system applicable to the monitoring system, and any kind of communication system such as a specific low-power wireless system and a communication system using weak radio waves may be adopted for the communication system of the invention.

In the embodiment of the invention, which is by no means limitative of the scope of the invention, the system incorporating the radio communication integrated circuit 21 and chip antenna 11 has two communication functions capable of performing one wireless communication between the paired biological information sensor modules 1 and another wireless communication between each biological information sensor module 1 and the host computer 29. However, these two communication functions of performing one wireless communication between the paired biological information sensor modules 1 and another wireless communication between each biological information sensor module 1 and the host computer 29 may be materialized severally by independent communication means. In this case, an appropriate communication system such as a Bluetooth system may be selectively used for each or all of the communication means in accordance with the application for short-distance wireless communication between the paired biological information sensor modules 1 or long-distance wireless communication between each biological information sensor module 1 and the host computer 29.

Figure 11:
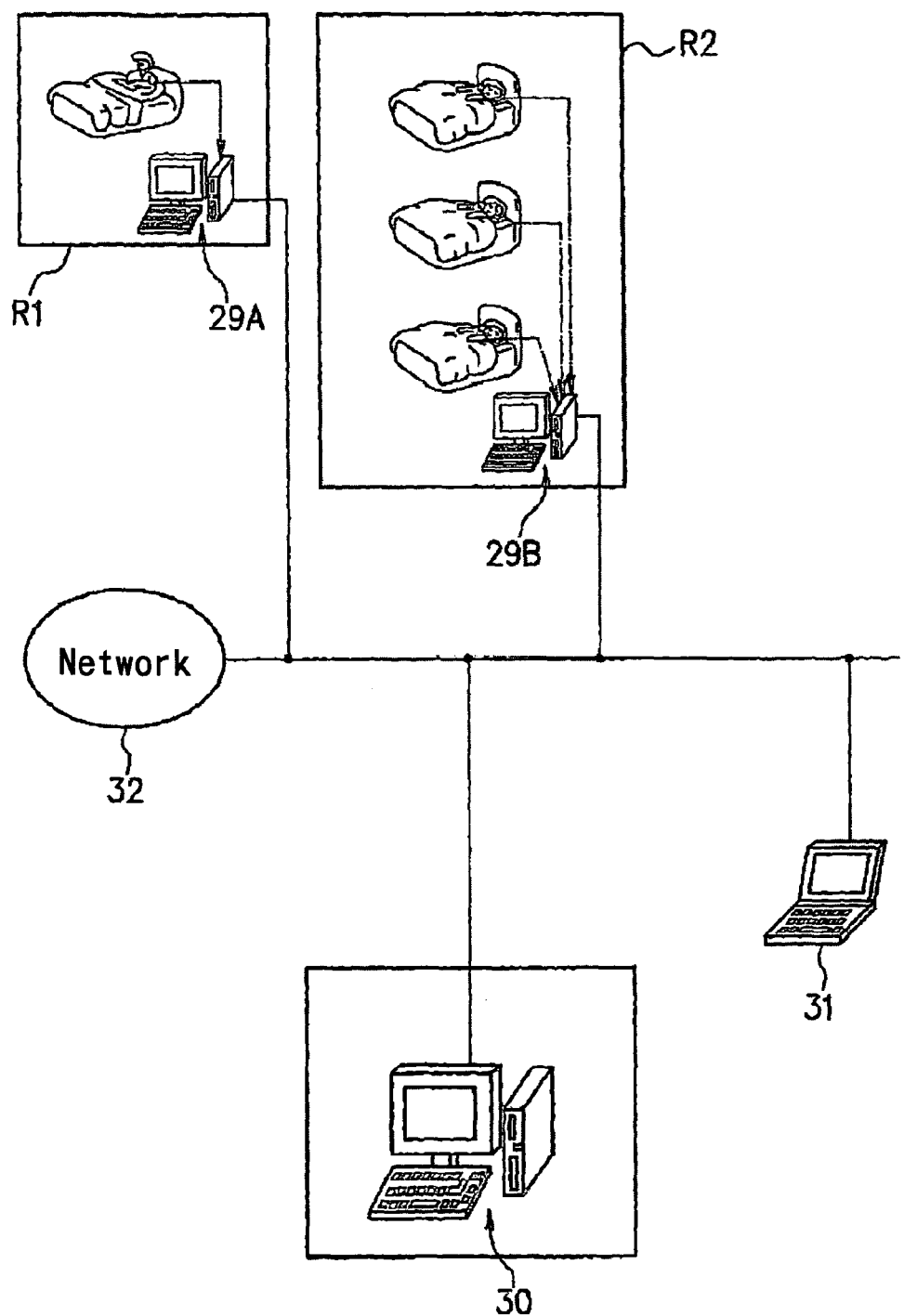
FIG. 11 is a schematic view showing another biological information monitoring system including the biological information sensor module shown in FIG. 1.

FIG. 11 illustrates one example of applying the biological information monitoring system of the invention to a large hospital. In this embodiment, the biological information monitoring system comprising the paired biological information sensor modules 1 attached to a subject to be monitored and the sub-host computer 29A is provided in a hospital room R1. Likewise in a hospital room R2, another biological information monitoring system comprising the paired biological information sensor modules 1 attached to a subject to be monitored and the sub-host computer 29B is provided. The sub-host computers 29A and 29B are connected to the main host computer 30 installed in a nurse station or research room for medical physicians through a wired or wireless LAN connection. In this system, the biological information data measured in the rooms R1 and R2 and the results of abnormality determination obtained in these rooms can be looked over by not only the sub-host computer 29A and 29B, but also the main host computer 30 in the nurse station or research room for medical physicians without going off to the rooms R1 and R2. For instance, by connecting a laptop computer 31 to the LAN connected to the communication network of the hospital, the biological information data and the results of abnormality determination obtained in the rooms R1 and R2 can also be viewed anyplace. This means that the biological information data and the results of abnormality determination can be viewed anywhere by accessing the communication network of the hospital, but it is desirable to authenticate the ID and/or password of an accessor to the communication network as a matter of course, specifically when building a large-scale communication system. The invention is not to be considered limited only to the number of hospital rooms and the formation of the communication network.

Figure 9:
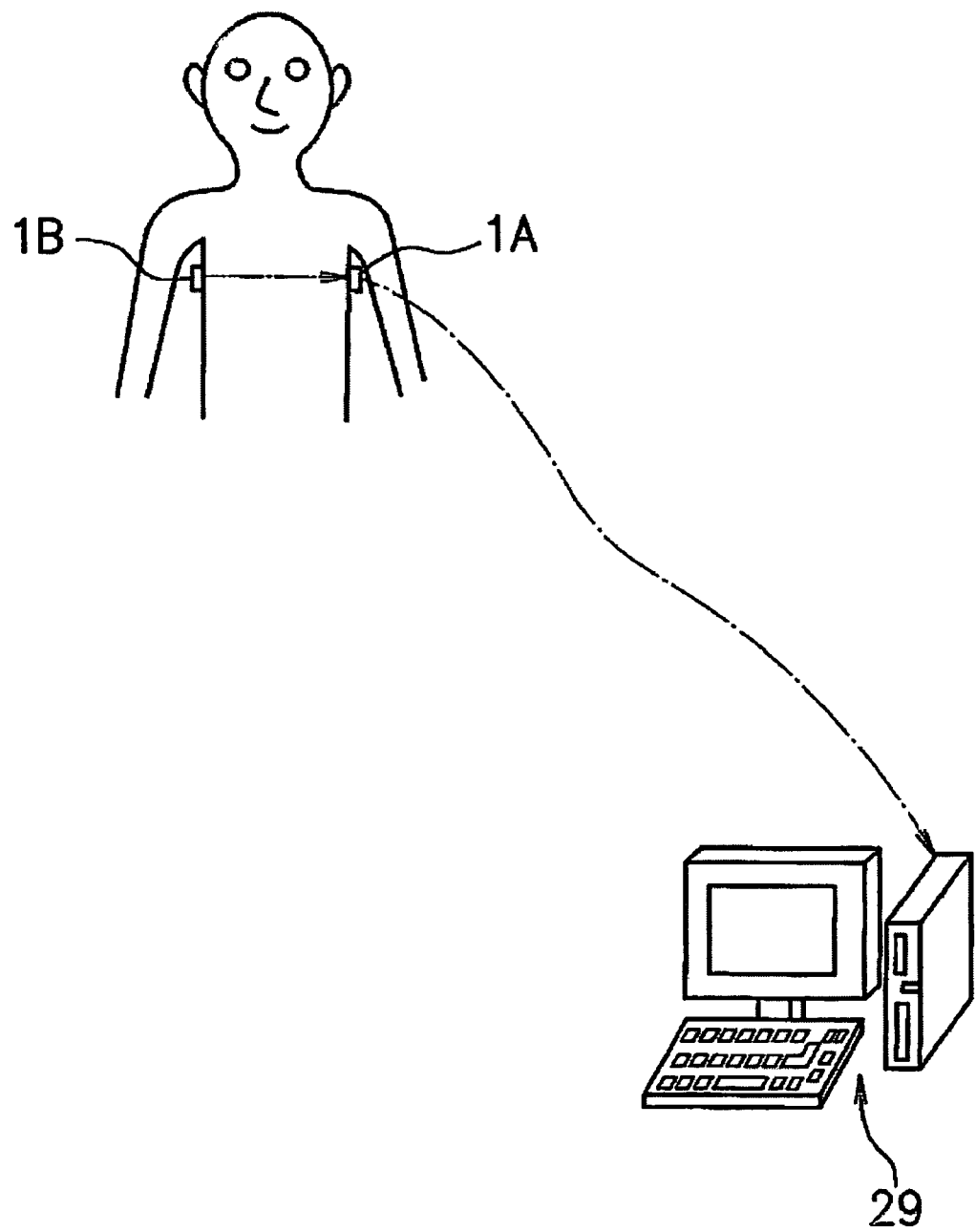
FIG. 9 is a schematic view showing a biological information monitoring system including the biological information sensor module shown in FIG. 1.
Figure 10:
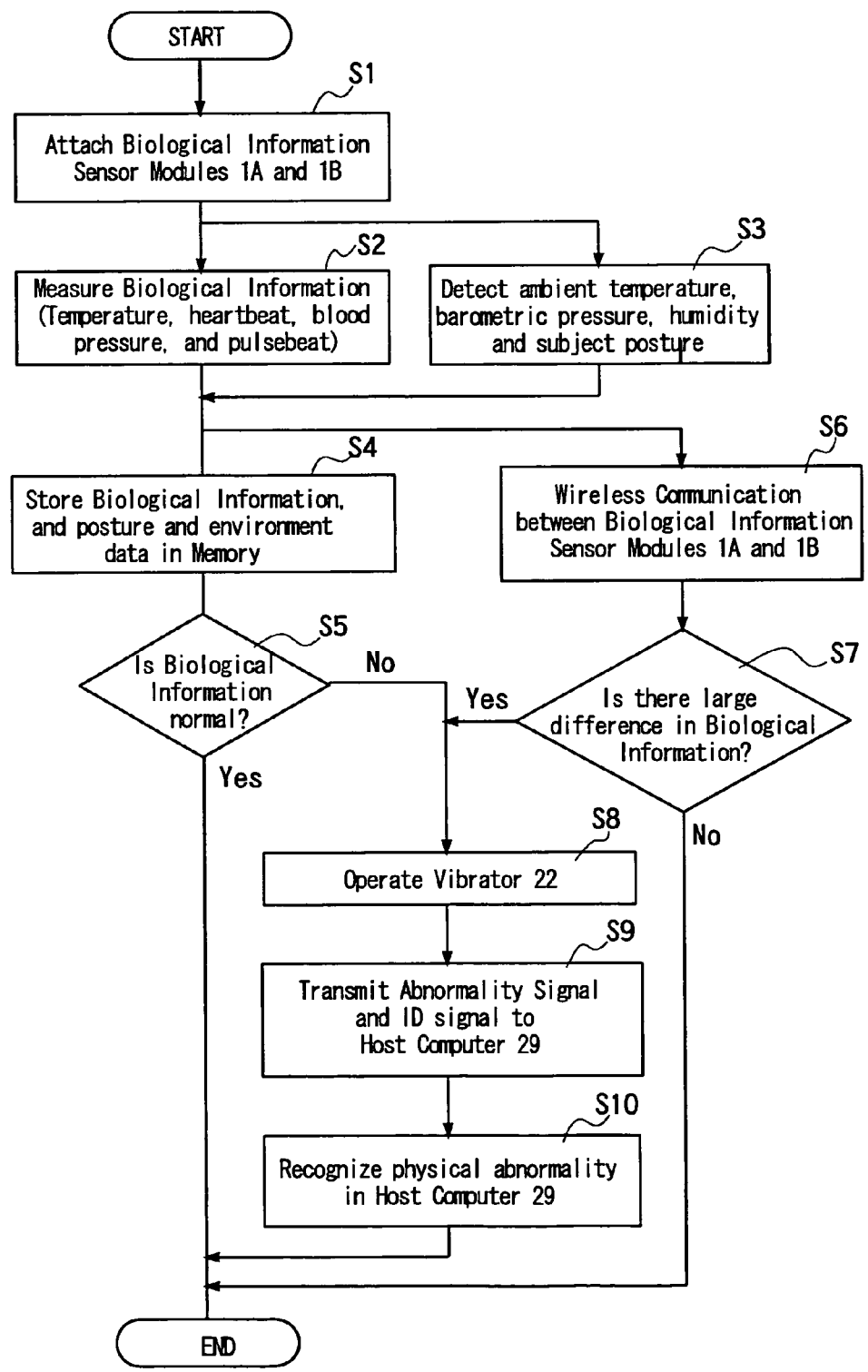
FIG. 10 is a flowchart of the schematic processing of the biological information monitoring system shown in FIG. 9.
Figure 12:
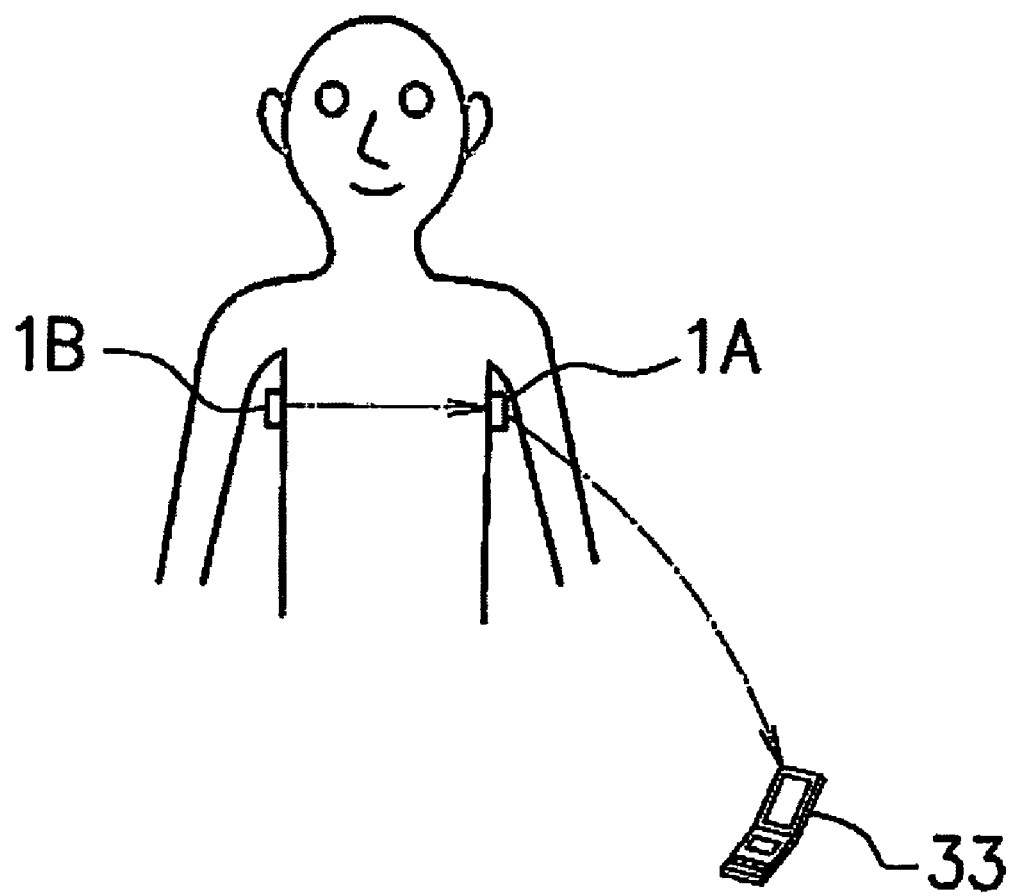
FIG. 12 is a schematic view showing still another biological information monitoring system including the biological information sensor module shown in FIG. 1.

A personal digital assistance (PDA) 33 may be used in place of the host computer 29 as shown in FIG. 12, or connected parallel to the host computer 29 as shown in FIG. 9. This PDA 33 can be carried and handled by anyone of the subject being monitored, subject's family, care personnel, physician and nurse. Even the easy-to-use PDA can perform all or part of the functions of the aforementioned host computer 29 at various places by being operated by the subject being monitored, subject's family and others, but also in this case, it is desirable to authenticate the ID and/or password of an accessor to the communication network.

Figure 14:
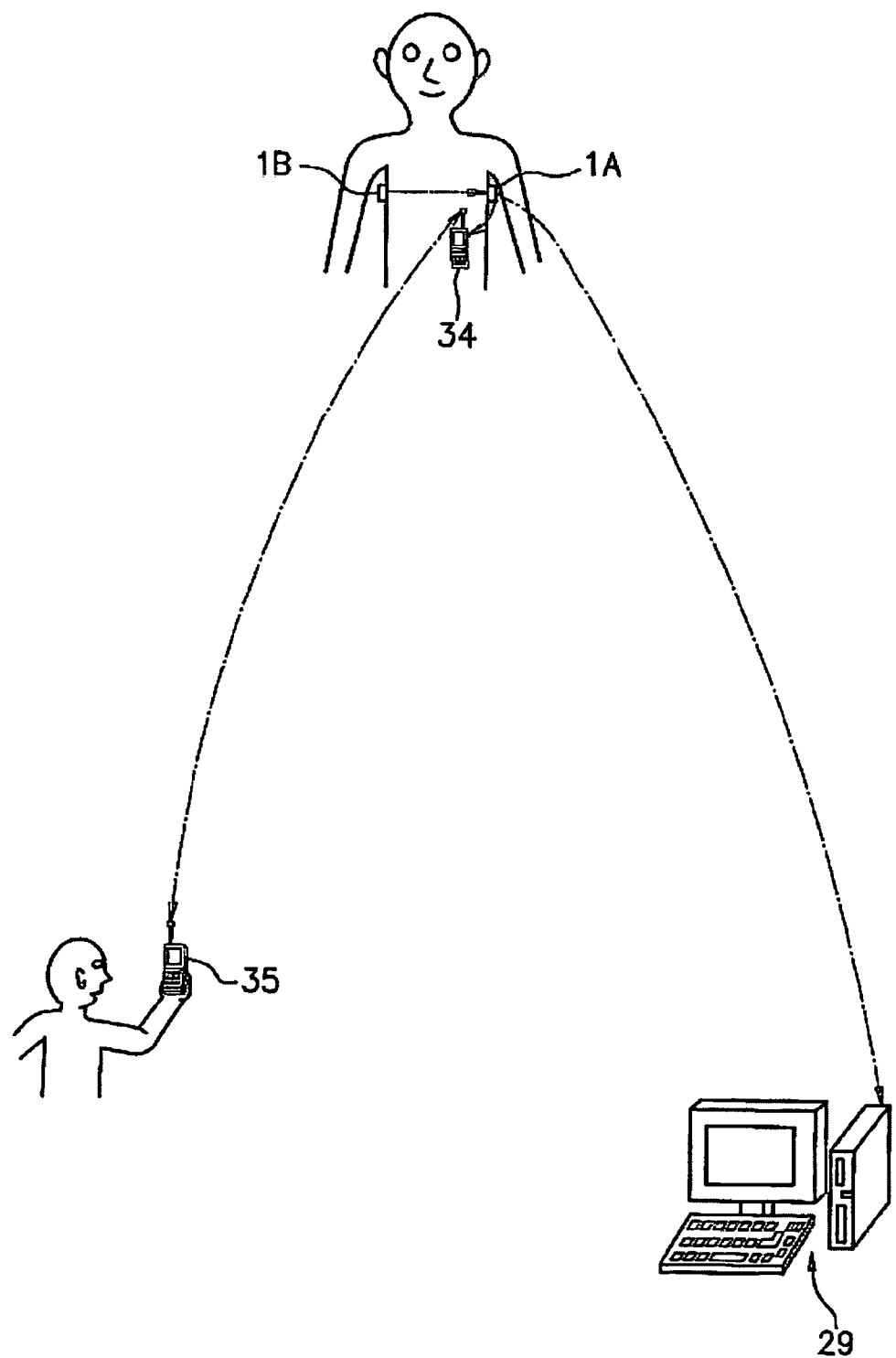
FIG. 14 is a schematic view showing the other biological information monitoring system including the biological information sensor module shown in FIG. 1.

In place of the PDA 33, a cell phone 34 of the subject to be monitored may be effectively utilized as shown in FIG. 14, in such a manner that, when any physical abnormality is detected by the biological information sensor module 1 attached to the subject, the CPU of the main integrated circuit 20 operates the cell phone 34 to automatically call the predetermined phone number (e.g. phone number of the cell phone 35 of subject's family, physician or nurse in charge), to make occurrence of the abnormality known to the relevant person with predetermined warning voice or sound. Thus, the physician, nurse and subject's family, even away from the subject being monitored, can instantly recognize the physical abnormality involved in the subject with the warning voice or sound. Therefore, even when the subject being monitored falls down due to the physical abnormality, the warning can be given automatically to the relevant person. Conversely, when the relevant person such as the physician, nurse or subject's family gets in contact with the cell phone 34 to issue any significant signal to the cell phone, various data (e.g. biological information detected by the module) stored in the memory of the main integrated circuit 20 in the biological information sensor module 1 are retrieved from the memory and given to the relevant person through the cell phone 34. If the cell phone 34 is provided with a GPS function, the location of the subject can be recognized concurrently. The location of the subject may be consecutively memorized in the memory to have a traceable function capable of recognizing the moving trajectory of the subject.

Figure 13:
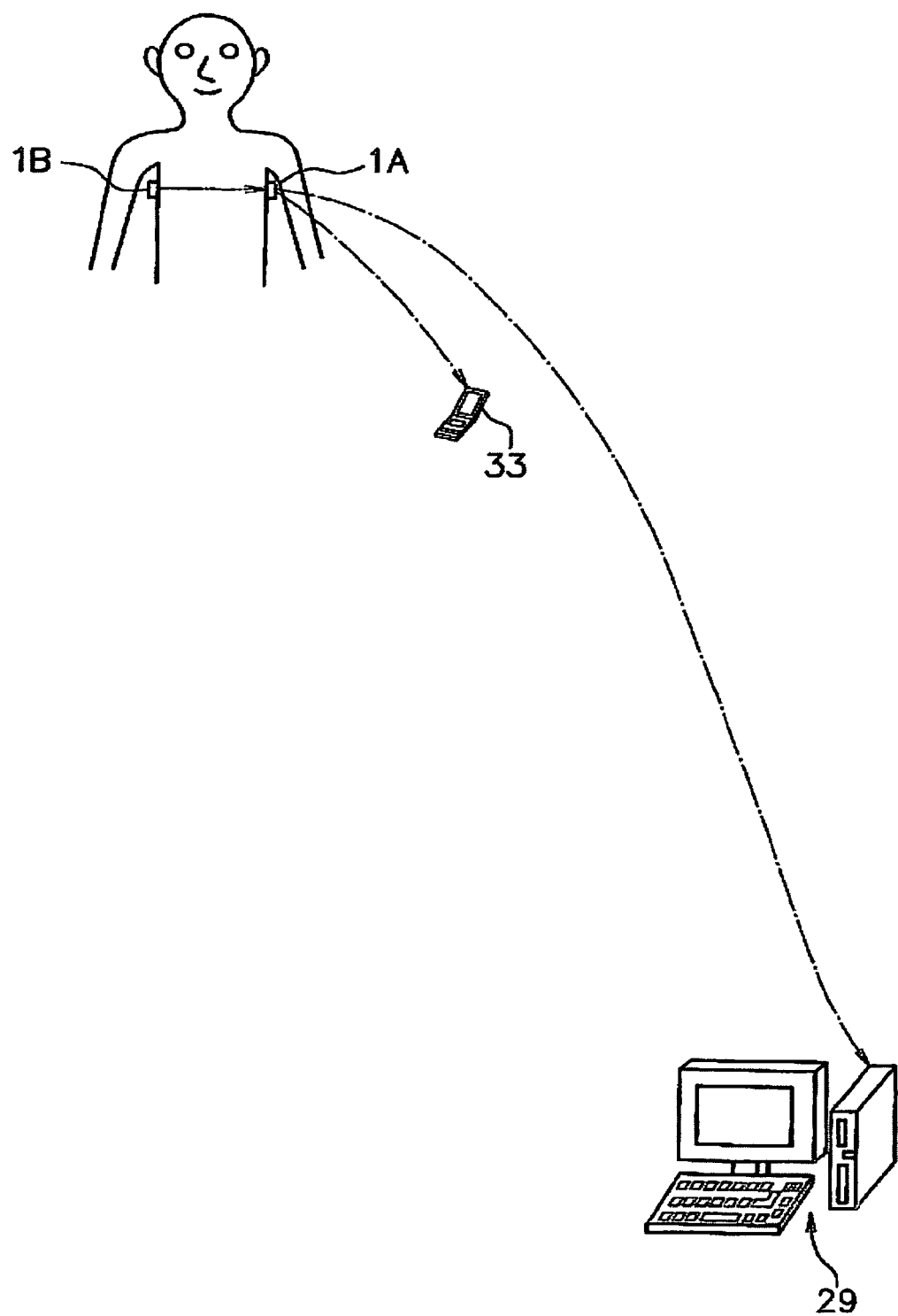
FIG. 13 is a schematic view showing yet another biological information monitoring system including the biological information sensor module shown in FIG. 1.

Of course, the biological information monitoring system of the invention can be formed by combining unrestrainedly the large-scale network system shown in FIG. 11, the PDA 33 shown in FIGS. 12 and 13, and the cell phone shown in FIG. 14.

Figure 5:
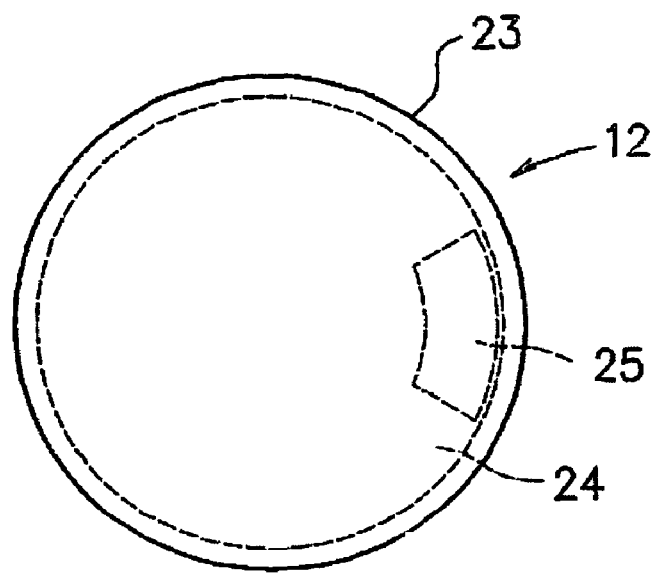
FIG. 5 is a plan view showing a tilt sensor in the biological information sensor module shown in FIG. 1.
Figure 6:
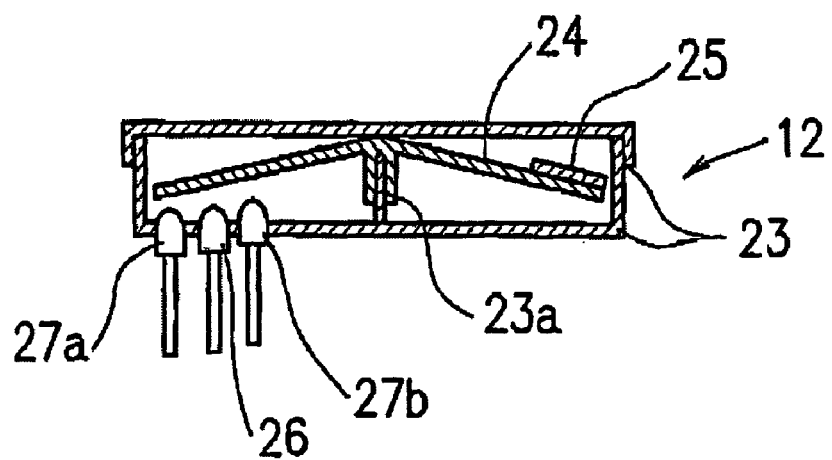
FIG. 6 is a front cross section of the tilt sensor shown in FIG. 5.
Figure 15:
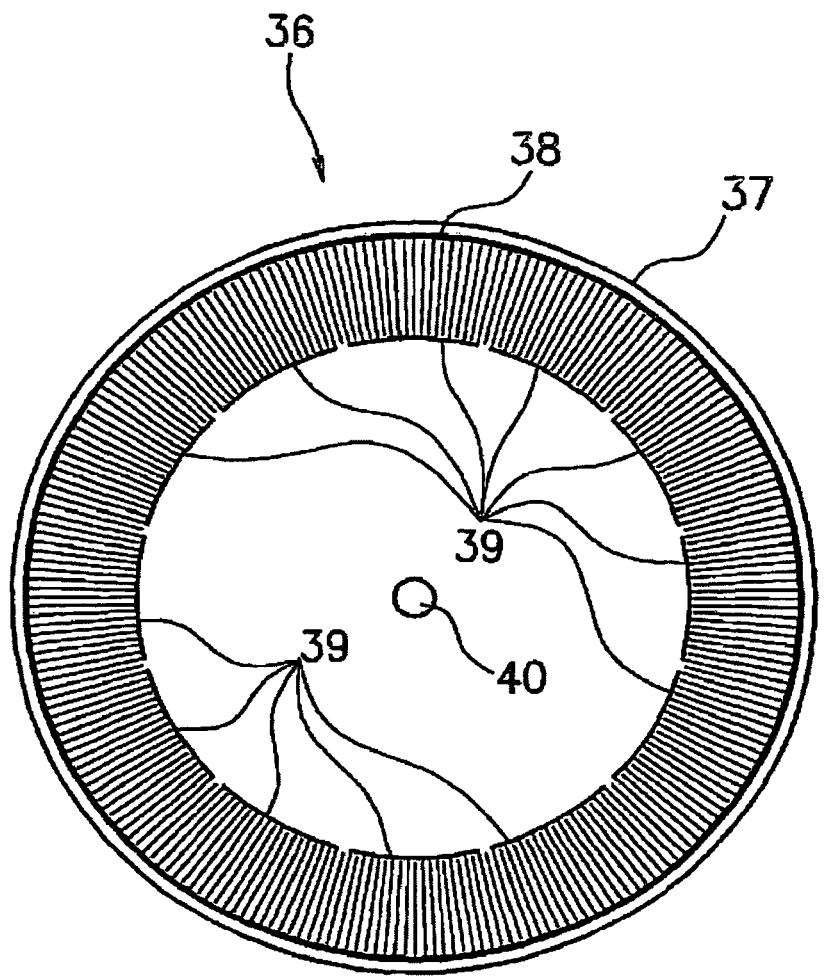
FIG. 15 is a plan view showing the interior of the tilt sensor in another embodiment.
Figure 16:
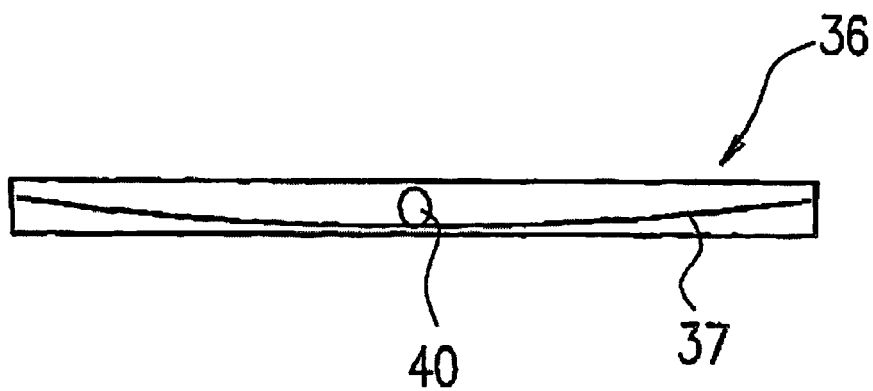
FIG. 16 is a front cross section of the tilt sensor of FIG. 15.

Also, the tilt sensor in the sensor module of the invention is not limitative in structure. For example, the tilt sensor 36 shown in FIGS. 15 and 16 may be used in place of the tilt sensor 12 shown in FIG. 5. The tilt sensor 36 has a common conductive section 32 formed in a circle on a shallow concave surface 37 and electrically independent conductive elements 39. The conductive section 32 and the conductive elements 39 are each formed in a comb and arranged in an interdigital pattern in nonconducting relationships to one another. On the shallow concave surface 37, a spherical conductor 40 (e.g. mercury drop conductor) is placed in a freely movable state. Thus, following tilting of the tilt sensor 36, the spherical conductor 40 moves along the shallow concave surface 37 in the tilting direction and establishes electric continuity between the conductive section 32 and one of the conductive elements 39 where the spherical conductor 40 is at rest on the shallow concave surface 37. The conductive element 39 coming into electric connection with the conductive section 32 can be detected by using a not-illustrated control device, to thereby recognize where the spherical conductor 40 is at rest on the shallow concave surface 37. As a result, the inclination of the tilt sensor 36 can be perceived. Even when the adjacent conductive elements 39 concurrently come in electric connection with the conductive section 32 through the spherical conductor 40, the position of the spherical conductor 40 and the inclination of the tilt sensor 36 can be perceived. When using the tilt sensor 36 in place of the tilt sensor 12 shown in FIG. 3, a high accuracy in measuring the inclination may not necessarily be required for the tilt sensor 36, but when requiring higher accuracy of measurement, the conductive section 32 and the conductive elements may be subdivided more minutely so as to improve the accuracy of the inclination measurement.

The practical use applications of the aforementioned biological information monitoring system of the invention will be described hereinafter.

[First Use Application]

As the first use application of the monitoring system of the invention, it may be applied for detecting the biological information such as the body temperature, heartbeat, blood pressure and pulse of the subject to be monitored, to make a diagnosis of physical abnormalities. The diagnosis is applicable to not only a subject suspected of having any physical abnormality, but also a healthy person. Furthermore, the monitoring system of the invention is suitable for preventive medical care to enable early recognition and treatment in prompt response to occurrence of the physical abnormality which is detected through the biological observation conducted continuously over a long period of time by use of the monitoring system of the invention. The use application of monitoring the latter healthy person makes a contribution especially to an elderly person who is living alone or a handicapped person. For example, on occasions when such a subject to be monitored encounters any abnormalities or difficulties with which the subject alone cannot cope, the abnormalities or difficulties can be promptly reported to the physician, nurse, subject's family or care personnel through the medium of the host computer 29, PDA 33 and/or cell phone 34 as described above.

Moreover, the biological information monitoring according to the invention can be carried out with ease and at low cost, and the monitoring system therefor can easily be handled by a person other than the physician or nurse, namely, it can readily be operated by even the subject being monitored, subject's family or care personnel.

In particular, the biological information monitoring according to the invention is effective for observation of a patient suffering a stroke, cardiac infarction or hepatic disease on the basis of the biological information such as the body temperature on the right and left sides of the patient's body. This is because, in the case of such diseases, the right and left sides of the patient's body are often deemed to be different in pulsebeat.

[Second Use Application]

As the second use application of the monitoring system of the invention, it may be applied for detecting the biological information such as the body temperature, heartbeat, blood pressure and pulse of the subject to be monitored, to investigate whether or not the environmental conditions where the subject undergoes an examination is suitable for the subject body. For instance, in a case where the subject is in a low-temperature environment for a long period of time, the monitoring of the biological information with the monitoring system provides an indication to the subject being monitored that it is time to get out of the harsh environment before damage occurs. Just as one example, when a significant difference occurring between the body temperatures measured on the right and left sides of a mountain climber exceeds the range of normal human body temperature, the monitoring system of the invention can call attention to the climber to abandon a climb and go down a mountain. Further, there may be another potential use of the monitoring system of the invention such that, when the difference in biological information such as body temperature, pulsebeat and blood pressure between the right and left sides of the subject body varies from a prescribed normal range, the subject may possibly be diagnosed as having a threat of cerebral embolism, such that care should be taken not to move the subject with suspected cerebral embolism.

Further, there may be still another potential use of the monitoring system of the invention such that, when a difference in biological information such as pulsebeat between the right and left sides of an exerciser getting exercise (training) exceeds the prescribed normal range, the monitoring system of the invention can call attention to the exerciser to discontinue the exercise. As another use application of the monitoring system of the invention, it may be used for perceiving the body conditions of a worker before and after work to determine whether the worker can fulfill a specific work operation. This use application is better suited for a long-distance truck driver, pilot, athlete and so on.

Since the monitoring system of this type is not infrequently applied to a healthy subject who is little connected with medical experts in these use applications, it can be effectively used lightly by the subject or subject's family. Thus, the biological information monitoring system of the invention has the advantage of being able to readily detect continuously the biological information for a prolonged period.

[Third Use Application]

Although associated with the first and second use applications described above, the predisponency of the biological information of the subject being monitored can be recognized.

That is, the biological information monitoring system of the invention can be applied to know the degree of recovery of a subject suffering from any disability during rehabilitation. For instance, a patient paralyzed on one side of the body in the fair convalescent stage has a small difference in body temperature between the body temperatures on both body sides of the patient. Also, a patient even not half-paralyzed but getting off balance in physical condition can recognize whether the off-balance is improved or not by using the biological information monitoring system of the invention, so that approach to treatment may be changed when the symptom is little improved, to allow the best treatment therefor to be chosen.

Practice Example

Next, a practical example applied to measure the biological information by using the aforementioned biological information monitoring system of the invention will be described.

Figure 17:
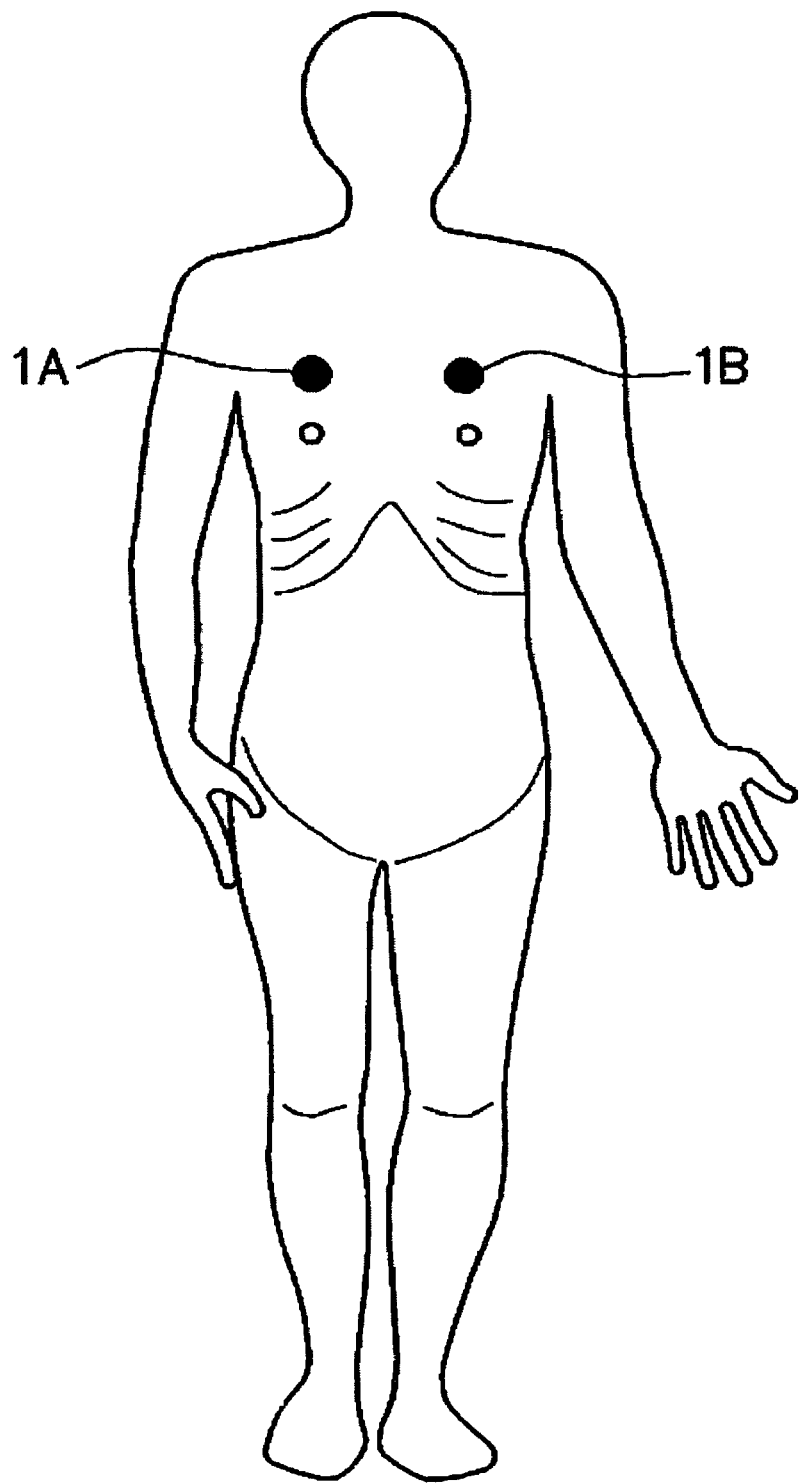
FIG. 17 shows the state in which the biological information sensor module of the invention is attached to the subject body.

At the outset of the measurement, a pair of biological information sensor modules 1A and 1B shown in FIG. 1 were attached to the upper papillary area of a subject to be inspected (46 years old male) as illustrated in FIG. 17. The biological information sensor modules 1A and 1B each incorporates a temperature sensor and communication means (or communicator) capable of transmitting measured data to the external computer by wireless.

Figure 18:
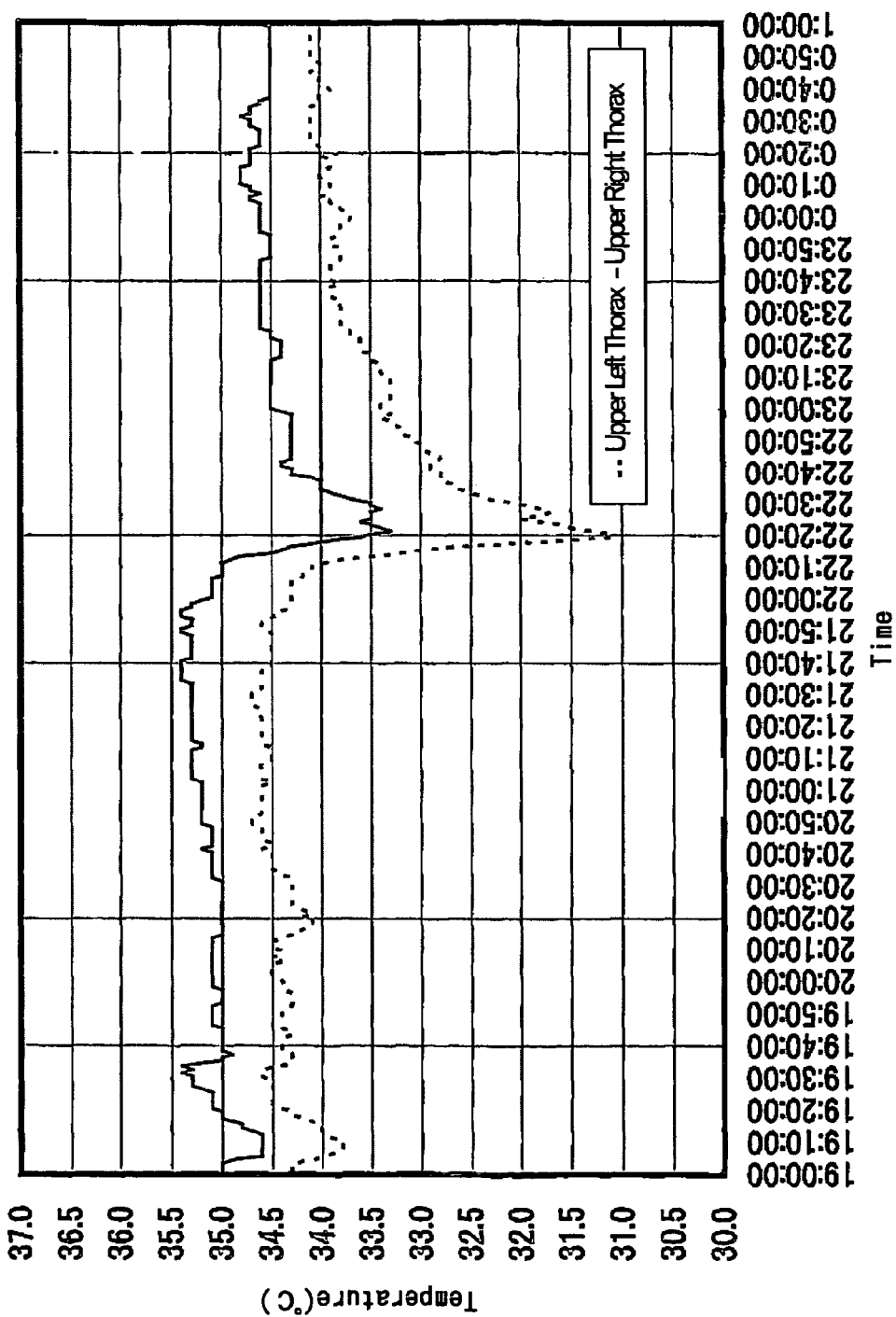
FIG. 18 is a graph showing a measurement result in one embodiment of the invention.
Figure 19:
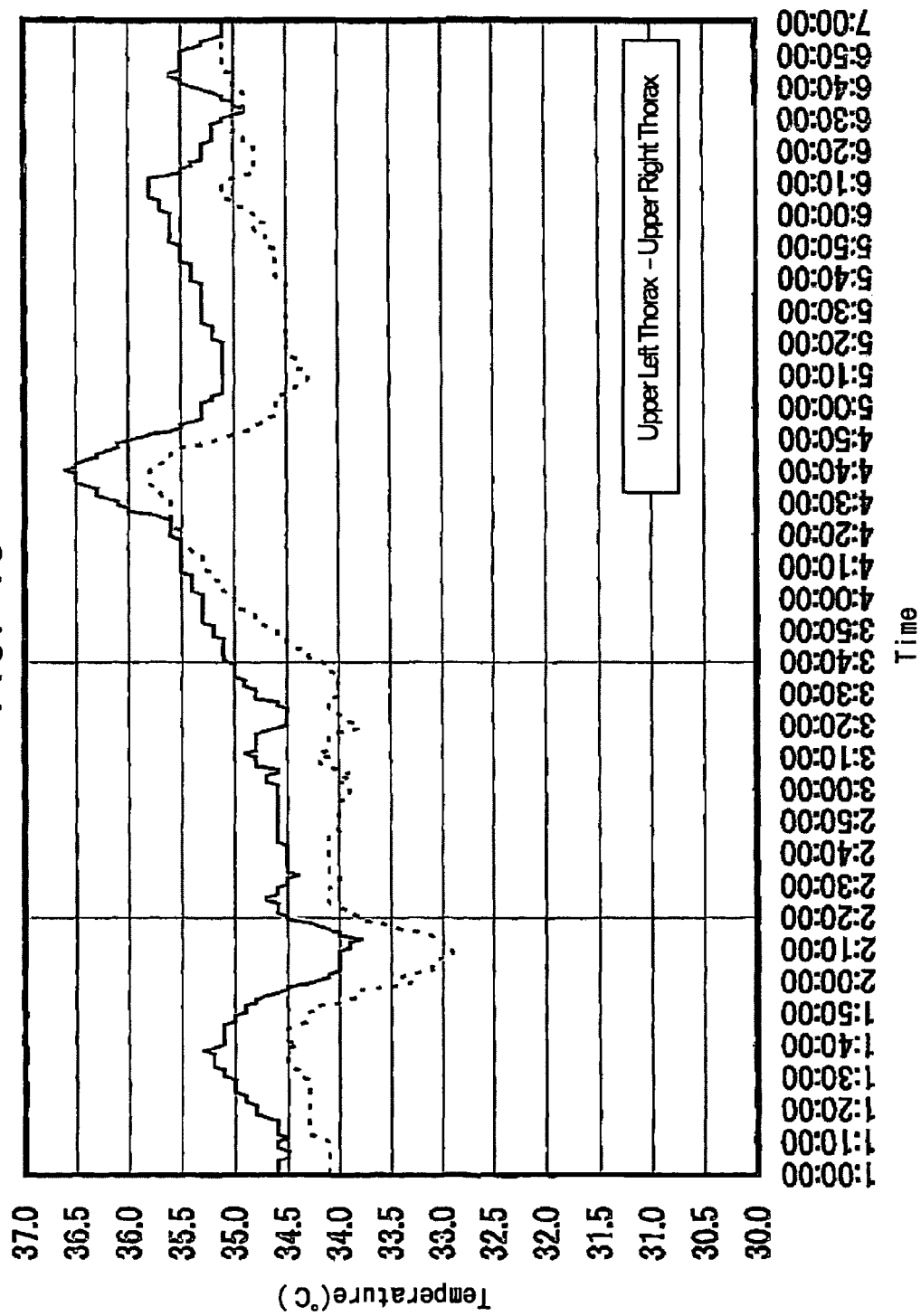
FIG. 19 is a graph showing a measurement result in another embodiment of the invention.

The body temperature measurement was carried out during the period of 7 pm to 7 am on the following morning and observed by the external computer. The measurement results thereof are shown in FIGS. 18 and 19. Incidentally, the subject got to bed at 3:20 am.

The actual measurement conducted in the foregoing manner showed that, when the difference between the body temperatures on the right and left sides of the subject body exceeded 0.5° C., a caution signal indicating occurrence of an abnormality was transmitted to the host computer by wireless and could be confirmed on the host computer, as shown in FIGS. 18 and 19. The measurement results attest that the monitoring system of the invention is effective in observing the biological information.

INDUSTRIAL APPLICABILITY

The biological information monitoring system according to the invention makes determination of physical abnormalities based on the difference in the biological information detected by the biological information sensors to the multiple loci on the right and left sides of a subject body and can facilitate early detection of the physical abnormalities, which has never been realized by conventional monitoring systems. Besides, the monitoring system of the invention can spectacularly increase the safety of medical treatment including monitoring of the biological information.

The invention claimed is:

1. A biological information monitoring system comprising a plurality of biological information sensor modules including a first biological information sensor module adapted to be attached to one of a right side and a left side of a subject body and a second biological information sensor module adapted to be attached to another of the right side and the left side of the subject body,
    wherein said first biological information sensor module includes:
        a first biological information sensor including a first pulse sensor for detecting first biological information including a first pulse; and
        a first communicator configured to wirelessly receive and transmit the first biological information,
    wherein said second biological information sensor module includes:
        a second biological information sensor including a second pulse sensor for detecting second biological information including a second pulse; and
        a second communicator configured to wirelessly receive and transmit the second biological information,
    wherein said first biological information sensor module includes an integrated circuit including a measurement calculating unit configured to detect an abnormality by comparing the first biological information including the first pulse and detected by said first biological information sensor with the second biological information including the second pulse, detected by said second biological information sensor, and wirelessly transmitted from said second communicator to said first biological information sensor module, and
    wherein said measurement calculating unit is configured to detect an abnormality related to a pulse difference only when the comparison performed by said measurement calculating unit identifies the pulse difference, between the first pulse and the second pulse, to be equal to or greater than 7 beats per minute.

2. The biological information monitoring system set forth in claim 1, wherein at least one of said first biological information sensor module and said second biological sensor module includes a memory for storing a determination result of the comparison received from said measurement calculating unit.

3. The biological information monitoring system set forth in claim 1, wherein said biological information monitoring system further comprises a warning unit for issuing a warning when said measurement calculating unit detects the abnormality related to the pulse difference.

4. The biological information monitoring system set forth in claim 1,
wherein at least one of said biological information sensor modules includes a communicator for communicating with an external electronic device to wirelessly transmit a determination result of the comparison performed by said measurement calculating unit, and
wherein said biological information monitoring system comprises the external electronic device for receiving the determination result wirelessly transmitted from said communicator.

5. The biological information monitoring system set forth in claim 4,
wherein each said plurality of biological information sensor modules includes said communicator for communicating with the outside to wirelessly transmit the determination result,
wherein each respective communicator of said plurality of biological information sensor modules wirelessly transmits a respective identification signal for distinguishing individual living subjects each having a respective biological information sensor module of the plurality of biological information sensor modules, and the determination result, and
wherein said external electronic device analyzes each respective identification signal and the determination result transmitted from each respective communicator, so as to identify the individual living subjects.

6. The biological information monitoring system set forth in claim 1,
wherein said first biological information sensor includes a first body temperature sensor for detecting a first body temperature and said second biological information sensor includes a second body temperature sensor for detecting a second body temperature, and
wherein said measurement calculating unit is configured to detect an abnormality related to a temperature difference only when the comparison performed by said measurement calculating unit identifies the temperature difference, between the first body temperature and the second body temperature, to be equal to or greater than 0.5° C.

7. The biological information monitoring system set forth in claim 1,
wherein said first biological information sensor includes a first blood pressure sensor for detecting a first blood pressure and said second biological information sensor includes a second blood pressure sensor for detecting a second blood pressure, and
wherein said measurement calculating unit is configured to detect an abnormality related to a blood pressure difference only when the comparison performed by said measurement calculating unit identifies the blood pressure difference, between the first blood pressure and the second blood pressure, to be equal to or greater than 10 mmHg.

* * * * *